(12) United States Patent
Allam et al.

(10) Patent No.: US 11,891,950 B2
(45) Date of Patent: Feb. 6, 2024

(54) SYSTEMS AND METHODS FOR POWER PRODUCTION WITH INTEGRATED PRODUCTION OF HYDROGEN

(71) Applicant: 8 RIVERS CAPITAL, LLC, Durham, NC (US)

(72) Inventors: Rodney John Allam, Chippenham (GB); Navid Rafati, Durham, NC (US)

(73) Assignee: 8 Rivers Capital, LLC, Durham, NC (US)

( * ) Notice: Subject to any disclaimer, the term of this patent is extended or adjusted under 35 U.S.C. 154(b) by 0 days.

(21) Appl. No.: 17/971,128

(22) Filed: Oct. 21, 2022

(65) Prior Publication Data

US 2023/0042457 A1 Feb. 9, 2023

Related U.S. Application Data

(63) Continuation of application No. 15/807,803, filed on Nov. 9, 2017, now Pat. No. 11,506,122.
(Continued)

(51) Int. Cl.
*F02C 6/18* (2006.01)
*F01K 23/10* (2006.01)
(Continued)

(52) U.S. Cl.
CPC .............. *F02C 6/18* (2013.01); *B01D 53/047* (2013.01); *B01J 7/00* (2013.01); *B01J 7/02* (2013.01);
(Continued)

(58) Field of Classification Search
CPC ...... F02C 3/14; F02C 3/20; F02C 3/30; F02C 3/34; F02C 6/18; F05D 2260/61; Y02E 20/16; B01D 53/047; B01D 2256/16; B01D 2257/108; C01B 2203/0216; C01B 2203/0233; C01B 2203/0255; C01B 2203/0261; C01B 2203/04; C01B 2203/047; C01B 2203/0475
See application file for complete search history.

(56) References Cited

U.S. PATENT DOCUMENTS 4,185,456 A 1/1980 Cummings
4,498,289 A 2/1985 Osgerby
(Continued)

FOREIGN PATENT DOCUMENTS

DE 10 2009 032 718 2/2011
JP 2008243594 10/2008
(Continued)

*Primary Examiner* — Arun Goyal
(74) *Attorney, Agent, or Firm* — Womble Bond Dickinson (US) LLP

(57) ABSTRACT

The present disclosure relates to systems and methods useful for power production. In particular, a power production cycle utilizing $CO_2$ as a working fluid may be configured for simultaneous hydrogen production. Beneficially, substantially all carbon arising from combustion in power production and hydrogen production is captured in the form of carbon dioxide. Further, produced hydrogen (optionally mixed with nitrogen received from an air separation unit) can be input as fuel in a gas turbine combined cycle unit for additional power production therein without any atmospheric $CO_2$ discharge.

21 Claims, 3 Drawing Sheets

Related U.S. Application Data

(60) Provisional application No. 62/419,552, filed on Nov. 9, 2016.

(51) Int. Cl.
| | | |
|---|---|---|
| *F01K 13/00* | (2006.01) | |
| *C07C 29/00* | (2006.01) | |
| *F02C 3/22* | (2006.01) | |
| *F02C 3/28* | (2006.01) | |
| *C10K 3/04* | (2006.01) | |
| *B01D 53/047* | (2006.01) | |
| *B01J 7/00* | (2006.01) | |
| *B01J 7/02* | (2006.01) | |
| *C01B 3/36* | (2006.01) | |
| *C01B 3/38* | (2006.01) | |
| *C01B 3/48* | (2006.01) | |
| *C01B 3/56* | (2006.01) | |
| *F02C 3/34* | (2006.01) | |

(52) U.S. Cl.
CPC ............... *C01B 3/36* (2013.01); *C01B 3/382* (2013.01); *C01B 3/48* (2013.01); *C01B 3/56* (2013.01); *C07C 29/00* (2013.01); *C10K 3/04* (2013.01); *F01K 13/00* (2013.01); *F01K 23/10* (2013.01); *F02C 3/22* (2013.01); *F02C 3/28* (2013.01); *F02C 3/34* (2013.01); *B01D 2256/16* (2013.01); *B01D 2257/502* (2013.01); *B01D 2257/504* (2013.01); *B01D 2259/402* (2013.01); *C01B 2203/0233* (2013.01); *C01B 2203/0244* (2013.01); *C01B 2203/0255* (2013.01); *C01B 2203/0261* (2013.01); *C01B 2203/0283* (2013.01); *C01B 2203/0288* (2013.01); *C01B 2203/042* (2013.01); *C01B 2203/043* (2013.01); *C01B 2203/047* (2013.01); *C01B 2203/0475* (2013.01); *C01B 2203/0495* (2013.01); *C01B 2203/0833* (2013.01); *C01B 2203/0838* (2013.01); *C01B 2203/0883* (2013.01); *C01B 2203/0894* (2013.01); *C01B 2203/1235* (2013.01); *C01B 2203/1241* (2013.01); *C01B 2203/141* (2013.01); *C01B 2203/142* (2013.01); *C01B 2203/146* (2013.01); *C01B 2203/84* (2013.01); *C10J 2300/1846* (2013.01); *F05D 2220/32* (2013.01); *F05D 2260/61* (2013.01); *Y02E 20/14* (2013.01); *Y02E 20/16* (2013.01); *Y02E 20/32* (2013.01)

(56) References Cited

U.S. PATENT DOCUMENTS

| | | | |
|---|---|---|---|
| 4,725,380 | A | 2/1988 | Pinto |
| 6,214,066 | B1 | 4/2001 | Nataraj et al. |
| 6,301,927 | B1 | 10/2001 | Reddy |
| 6,474,069 | B1 | 11/2002 | Smith |
| 6,500,241 | B2 | 12/2002 | Reddy |
| 6,534,551 | B2 | 3/2003 | Allam et al. |
| 6,932,958 | B2 | 8/2005 | Wangerow et al. |
| 6,946,016 | B2 | 9/2005 | Reddy |
| 6,966,171 | B2 | 11/2005 | Uematsu et al. |
| 7,056,480 | B2 | 6/2006 | Ogawa |
| 7,089,727 | B2 | 8/2006 | Schütz |
| 7,138,001 | B2 | 11/2006 | Knez et al. |
| 7,179,324 | B2 | 2/2007 | Baksh et al. |
| 7,182,917 | B2 | 2/2007 | Krueger |
| 7,182,921 | B2 | 2/2007 | Miura et al. |
| 7,192,569 | B2 | 3/2007 | Stewart |
| 7,220,505 | B2 | 5/2007 | Malhotra et al. |
| 7,247,656 | B2 | 7/2007 | Guo et al. |
| 7,252,692 | B2 | 8/2007 | Rei |
| 7,326,482 | B2 | 2/2008 | Haltiner, Jr. et al. |
| 7,341,609 | B2 | 3/2008 | DeVries |
| 7,393,382 | B2 | 7/2008 | Givens |
| 7,399,342 | B2 | 7/2008 | Bizjak |
| 7,404,846 | B2 | 7/2008 | Golden et al. |
| 7,419,648 | B2 | 9/2008 | Kuipers et al. |
| 7,427,368 | B2 | 9/2008 | Drnevich |
| 7,550,215 | B2 | 6/2009 | Malhotra et al. |
| 7,574,855 | B2 | 8/2009 | Benz et al. |
| 7,611,676 | B2 | 11/2009 | Inage et al. |
| 7,628,963 | B2 | 12/2009 | Woo et al. |
| 7,635,399 | B2 | 12/2009 | Su |
| 7,686,856 | B2 | 3/2010 | Hemmings et al. |
| 7,695,708 | B2 | 4/2010 | Peng et al. |
| 7,708,812 | B2 | 5/2010 | Shinkai et al. |
| 7,727,509 | B2 | 6/2010 | Abbott et al. |
| 7,731,935 | B2 | 6/2010 | Brady et al. |
| 7,763,086 | B2 | 7/2010 | Woods et al. |
| 7,763,098 | B2 | 7/2010 | Alizadeh-Khiavi et al. |
| 7,815,892 | B2 | 10/2010 | Hershkowitz et al. |
| 7,828,864 | B2 | 11/2010 | Edlund et al. |
| 7,833,311 | B2 | 11/2010 | Givens |
| 7,833,326 | B2 | 11/2010 | Bizjak |
| 7,837,765 | B2 | 11/2010 | Adams et al. |
| 7,837,973 | B2 | 11/2010 | Snyder et al. |
| 7,883,672 | B2 | 2/2011 | Woo et al. |
| 7,908,842 | B2 | 3/2011 | Eroglu et al. |
| 7,914,764 | B2 | 3/2011 | Hershkowitz et al. |
| 7,931,888 | B2 | 4/2011 | Drnevich et al. |
| 7,932,296 | B2 | 4/2011 | Malhotra et al. |
| 7,950,239 | B2 | 5/2011 | Lilley et al. |
| 7,960,441 | B2 | 6/2011 | Wolf |
| 7,985,399 | B2 | 7/2011 | Drnevich et al. |
| 7,988,948 | B2 | 8/2011 | Guvelioglu et al. |
| 8,021,464 | B2 | 9/2011 | Gauthier et al. |
| 8,025,862 | B2 | 9/2011 | Rojey et al. |
| 8,034,321 | B2 | 10/2011 | Mauthner et al. |
| 8,038,748 | B2 | 10/2011 | Edlund |
| 8,038,771 | B2 | 10/2011 | Bizjak |
| 8,070,841 | B2 | 12/2011 | Adams et al. |
| 8,080,070 | B2 | 12/2011 | Grover |
| 8,097,371 | B2 | 1/2012 | Suehiro et al. |
| 8,110,022 | B2 | 2/2012 | DeVries |
| 8,124,049 | B2 | 2/2012 | Grover |
| 8,137,422 | B2 | 3/2012 | Licht et al. |
| 8,177,868 | B2 | 5/2012 | Johnston |
| 8,187,363 | B2 | 5/2012 | Grover |
| 8,206,669 | B2 | 6/2012 | Schaffer et al. |
| 8,240,370 | B2 | 8/2012 | Palamara et al. |
| 8,257,452 | B2 | 9/2012 | Menzel |
| 8,257,668 | B2 | 9/2012 | Mukai et al. |
| 8,263,274 | B2 | 9/2012 | Sonnichsen et al. |
| 8,268,024 | B2 | 9/2012 | Price |
| 8,273,139 | B2 | 9/2012 | Malhotra et al. |
| 8,273,489 | B2 | 9/2012 | Ukai et al. |
| 8,287,763 | B2 | 10/2012 | Pham et al. |
| 8,303,930 | B2 | 11/2012 | Chen et al. |
| 8,375,723 | B2 | 2/2013 | Benz et al. |
| 8,394,174 | B2 | 3/2013 | Chen et al. |
| 8,414,666 | B2 | 4/2013 | Palamara et al. |
| 8,419,829 | B2 | 4/2013 | Wallace |
| 8,449,633 | B2 | 5/2013 | Pham et al. |
| 8,449,649 | B2 | 5/2013 | Greenough |
| 8,460,630 | B2 | 6/2013 | Niitsuma et al. |
| 8,486,180 | B2 | 7/2013 | Chen |
| 8,535,638 | B2 | 9/2013 | Terrien et al. |
| 8,551,217 | B2 | 10/2013 | Baksh et al. |
| 8,596,075 | B2 | 12/2013 | Allam et al. |
| 8,597,383 | B2 | 12/2013 | Pham et al. |
| 8,617,294 | B2 | 12/2013 | Adams et al. |
| 8,623,563 | B2 | 1/2014 | Anzai |
| 8,636,922 | B2 | 1/2014 | Grover et al. |
| 8,671,688 | B2 | 3/2014 | Rogers et al. |
| 8,673,135 | B2 | 3/2014 | Colyar et al. |
| 8,685,282 | B2 | 4/2014 | Iaquaniello |
| 8,685,358 | B2 | 4/2014 | Allam |
| 8,690,972 | B2 | 4/2014 | Takata et al. |
| 8,692,034 | B2 | 4/2014 | Han |
| 8,702,823 | B2 | 4/2014 | Kani et al. |

(56) References Cited

U.S. PATENT DOCUMENTS

| | | |
|---|---|---|
| 8,715,617 B2 | 5/2014 | Genkin et al. |
| 8,726,628 B2 | 5/2014 | Wichmann et al. |
| 8,747,498 B2 | 6/2014 | Taguchi et al. |
| 8,747,806 B2 | 6/2014 | Catchpole |
| 8,752,390 B2 | 6/2014 | Wright et al. |
| 8,769,961 B2 | 7/2014 | Allam |
| 8,771,637 B2 | 7/2014 | Wynn et al. |
| 8,776,532 B2 | 7/2014 | Allam et al. |
| 8,784,531 B2 | 7/2014 | Okada et al. |
| 8,790,618 B2 | 7/2014 | Adams et al. |
| 8,808,425 B2 | 8/2014 | Genkin et al. |
| 8,852,456 B2 | 10/2014 | Valentin et al. |
| 8,869,889 B2 | 10/2014 | Palmer et al. |
| 8,900,355 B2 | 12/2014 | White |
| 8,900,546 B2 | 12/2014 | Van De Graaf et al. |
| 8,916,304 B2 | 12/2014 | Tamura et al. |
| 8,926,866 B2 | 1/2015 | Kim et al. |
| 8,956,587 B1 | 2/2015 | Peng et al. |
| 8,959,887 B2 | 2/2015 | Allam et al. |
| 8,986,002 B2 | 3/2015 | Palmer et al. |
| 8,986,631 B2 | 3/2015 | Berggren et al. |
| 8,992,642 B2 | 3/2015 | Vik |
| 8,992,669 B2 | 3/2015 | Ideda et al. |
| 9,028,794 B2 | 5/2015 | Darde et al. |
| 9,040,011 B2 | 5/2015 | Filippi et al. |
| 9,061,911 B2 | 6/2015 | Azad |
| 9,062,608 B2 | 6/2015 | Allam et al. |
| 9,068,743 B2 | 6/2015 | Palmer et al. |
| 9,073,007 B2 | 7/2015 | Park et al. |
| 9,101,899 B2 | 8/2015 | Singh et al. |
| 9,126,172 B2 | 9/2015 | Singh et al. |
| 9,132,402 B2 | 9/2015 | Singh et al. |
| 9,216,903 B2 | 12/2015 | McKenna et al. |
| 9,227,844 B2 | 1/2016 | Han et al. |
| 9,240,604 B2 | 1/2016 | Maenishi et al. |
| 9,242,206 B2 | 1/2016 | Okada et al. |
| 9,249,690 B2 | 2/2016 | Karni et al. |
| 9,260,303 B2 | 2/2016 | Filippi et al. |
| 9,309,130 B2 | 4/2016 | Peng et al. |
| 9,321,643 B2 | 4/2016 | Denis et al. |
| 9,321,655 B2 | 4/2016 | Singh et al. |
| 9,327,973 B1 | 5/2016 | Tsai et al. |
| 9,358,506 B2 | 6/2016 | Cheiky |
| 9,359,201 B2 | 6/2016 | Simakov et al. |
| 9,365,131 B2 | 6/2016 | Jamal et al. |
| 9,399,607 B2 | 7/2016 | Tsai et al. |
| 9,415,298 B1 | 8/2016 | Statzer |
| 9,416,728 B2 | 8/2016 | Palmer et al. |
| 9,493,350 B2 | 11/2016 | Morico et al. |
| 9,523,312 B2 | 12/2016 | Allam et al. |
| 9,550,671 B2 | 1/2017 | Darde et al. |
| 9,556,026 B1 | 1/2017 | Davis et al. |
| 9,556,027 B2 | 1/2017 | Chakmvarti et al. |
| 9,580,314 B2 | 2/2017 | Darde et al. |
| 9,583,776 B2 | 2/2017 | Thornton et al. |
| 9,586,819 B2 | 3/2017 | Xu et al. |
| 9,617,152 B2 | 4/2017 | Johnston |
| 9,637,427 B2 | 5/2017 | Tsai et al. |
| 9,685,672 B2 | 6/2017 | Iiyama et al. |
| 9,745,191 B2 | 8/2017 | Pham et al. |
| 9,776,862 B2 | 10/2017 | Fujisawa et al. |
| 9,776,863 B2 | 10/2017 | Iaquaniello et al. |
| 9,802,820 B2 | 10/2017 | Iaquaniello et al. |
| 9,806,364 B2 | 10/2017 | Jamal et al. |
| 9,869,245 B2 | 1/2018 | Allam et al. |
| 9,914,643 B2 | 3/2018 | Allam |
| 9,917,320 B2 | 3/2018 | Thornton et al. |
| 9,944,522 B2 | 4/2018 | Cheiky |
| 9,969,666 B1 | 5/2018 | Roesch et al. |
| 10,008,730 B2 | 6/2018 | Jamal et al. |
| 10,018,115 B2 | 7/2018 | Allam et al. |
| 10,046,673 B1 | 8/2018 | Allam et al. |
| 10,047,671 B2 | 8/2018 | Allam et al. |
| 10,066,870 B2 | 9/2018 | Klein |
| 10,071,909 B2 | 9/2018 | Beltmmini et al. |
| 10,093,542 B2 | 10/2018 | Beltmmini et al. |
| 10,131,593 B2 | 11/2018 | Okada et al. |
| 10,155,661 B2 | 12/2018 | Kang et al. |
| 10,160,704 B2 | 12/2018 | Roesch et al. |
| 10,218,020 B2 | 2/2019 | Jamal et al. |
| 10,246,326 B2 | 4/2019 | Chlapik et al. |
| 10,252,910 B2 | 4/2019 | Beltmmini et al. |
| 10,252,911 B2 | 4/2019 | Beltmmini et al. |
| 10,256,489 B2 | 4/2019 | Kakuwa et al. |
| 10,281,203 B2 | 5/2019 | Guillard et al. |
| 10,283,795 B2 | 5/2019 | Jamal et al. |
| 10,288,346 B2 | 5/2019 | Guillard et al. |
| 10,302,357 B2 | 5/2019 | Hernandez et al. |
| 10,308,508 B2 | 6/2019 | Saloway |
| 10,370,248 B2 | 8/2019 | Kang et al. |
| 10,393,431 B2 | 8/2019 | Roesch et al. |
| 10,415,434 B2 | 9/2019 | Allam et al. |
| 10,422,252 B2 | 9/2019 | Allam et al. |
| 10,464,818 B2 | 11/2019 | Filippi et al. |
| 10,472,236 B2 | 11/2019 | Farace et al. |
| 10,533,494 B2 | 1/2020 | Xiao et al. |
| 10,549,991 B2 | 2/2020 | Wix et al. |
| 10,626,014 B2 | 4/2020 | Nicholson et al. |
| 10,633,313 B1 | 4/2020 | Roesch et al. |
| 10,634,048 B2 | 4/2020 | Forrest et al. |
| 10,634,425 B2 | 4/2020 | Guillard et al. |
| 10,662,127 B2 | 5/2020 | Beauchamp et al. |
| 10,703,629 B2 | 7/2020 | Saloway |
| 10,745,276 B2 | 8/2020 | Warta et al. |
| 10,746,461 B2 | 8/2020 | Allam |
| 10,849,714 B2 | 12/2020 | Lehtonen |
| 10,899,612 B2 | 1/2021 | Seo et al. |
| 10,919,761 B2 | 2/2021 | Lehmann et al. |
| 10,960,372 B2 | 3/2021 | Verykios et al. |
| 10,961,122 B2 | 3/2021 | Verykios et al. |
| 10,975,766 B2 | 4/2021 | Allam et al. |
| 10,988,379 B2 | 4/2021 | Fedorov et al. |
| 10,989,113 B2 | 4/2021 | Forrest et al. |
| 11,059,011 B2 | 7/2021 | Yukumoto et al. |
| 11,066,298 B2 | 7/2021 | Rafati et al. |
| 11,091,704 B2 | 8/2021 | Wegerer et al. |
| 11,130,676 B2 | 9/2021 | Nicholson et al. |
| 11,149,634 B2 | 10/2021 | Callahan |
| 11,149,636 B2 | 10/2021 | Callahan |
| 11,168,045 B2 | 11/2021 | Moreo |
| 11,174,208 B2 | 11/2021 | Beauchamp et al. |
| 11,174,759 B2 | 11/2021 | Allam et al. |
| 11,207,649 B2 | 12/2021 | Hoffman et al. |
| 11,208,323 B2 | 12/2021 | Forrest et al. |
| 11,213,795 B2 | 1/2022 | Hassler et al. |
| 11,231,224 B2 | 1/2022 | Allam et al. |
| 11,253,831 B2 | 2/2022 | Verykios et al. |
| 11,285,437 B2 | 3/2022 | Lu et al. |
| 11,305,250 B2 | 4/2022 | Verykios et al. |
| 11,345,593 B2 | 5/2022 | Mortensen |
| 11,351,517 B2 | 6/2022 | Ulber et al. |
| 11,383,978 B2 | 7/2022 | Verykios et al. |
| 11,434,133 B2 | 9/2022 | Song et al. |
| 11,441,838 B2 | 9/2022 | Vu et al. |
| 11,465,094 B2 | 10/2022 | Rah et al. |
| 11,479,462 B1 | 10/2022 | Spicer |
| 11,485,635 B2 | 11/2022 | Kawamoto et al. |
| 11,485,637 B2 | 11/2022 | Coleman et al. |
| 11,491,437 B2 | 11/2022 | Gary et al. |
| 11,491,456 B2 | 11/2022 | Ko |
| 11,492,254 B2 | 11/2022 | Harale et al. |
| 11,492,255 B2 | 11/2022 | Younes et al. |
| 11,506,122 B2 | 11/2022 | Allam et al. |
| 11,512,257 B1 | 11/2022 | Spicer et al. |
| 11,535,514 B2 | 12/2022 | Mays et al. |
| 11,554,955 B2 | 1/2023 | Tranier |
| 11,583,798 B2 | 2/2023 | Chai et al. |
| 11,583,824 B2 | 2/2023 | Harale et al. |
| 11,597,649 B2 | 3/2023 | Krishnamoorthy et al. |
| 11,607,657 B2 | 3/2023 | Verykios et al. |
| 11,608,266 B2 | 3/2023 | Moore et al. |
| 11,614,280 B2 | 3/2023 | Ko |
| 11,618,676 B2 | 4/2023 | Hill et al. |
| 2002/0004152 A1 | 1/2002 | Clawson et al. |

(56) References Cited

U.S. PATENT DOCUMENTS

| | | |
|---|---|---|
| 2005/0080146 A1 | 4/2005 | Abbott et al. |
| 2007/0130957 A1* | 6/2007 | Hoffmann ............... F02C 6/18 60/39.15 |
| 2007/0231244 A1 | 10/2007 | Shah et al. |
| 2010/0047160 A1 | 2/2010 | Allam |
| 2012/0277327 A1 | 11/2012 | Han et al. |
| 2012/0292574 A1 | 11/2012 | Terrien et al. |
| 2012/0301391 A1 | 11/2012 | Basini et al. |
| 2013/0205746 A1 | 8/2013 | Allam et al. |
| 2016/0363368 A1 | 12/2016 | Zanganeh et al. |
| 2018/0128172 A1 | 5/2018 | Allam |
| 2018/0363550 A1 | 12/2018 | Allam et al. |
| 2019/0135626 A1 | 5/2019 | Rafati et al. |
| 2019/0337801 A1 | 11/2019 | Ulber et al. |
| 2020/0172395 A1 | 6/2020 | Choi et al. |
| 2020/0307997 A1 | 10/2020 | Tranier |
| 2020/0368667 A1 | 11/2020 | Obata et al. |
| 2020/0406212 A1 | 12/2020 | Mortensen et al. |
| 2021/0139794 A1 | 5/2021 | Mukthiyar et al. |
| 2021/0155478 A1 | 5/2021 | Shrivastava et al. |
| 2021/0179425 A1 | 6/2021 | Ott |
| 2021/0252471 A1 | 8/2021 | Park |
| 2021/0300757 A1 | 9/2021 | Tadiello et al. |
| 2021/0323818 A1 | 10/2021 | Rafati et al. |
| 2021/0395085 A1 | 12/2021 | Paglieri et al. |
| 2022/0040626 A1 | 2/2022 | Coleman et al. |
| 2022/0048768 A1 | 2/2022 | Schmidt et al. |
| 2022/0089437 A1 | 3/2022 | Shrivastava et al. |
| 2022/0099003 A1 | 3/2022 | Lu et al. |
| 2022/0136700 A1 | 5/2022 | Strand et al. |
| 2022/0143549 A1 | 5/2022 | Bauer et al. |
| 2022/0144634 A1 | 5/2022 | Schmidt et al. |
| 2022/0168687 A1 | 6/2022 | Hill |
| 2022/0169500 A1 | 6/2022 | Ko |
| 2022/0169501 A1 | 6/2022 | Matsuo et al. |
| 2022/0185666 A1 | 6/2022 | Streb et al. |
| 2022/0194789 A1 | 6/2022 | Christensen et al. |
| 2022/0203297 A1 | 6/2022 | Lu et al. |
| 2022/0212925 A1 | 7/2022 | Albuali et al. |
| 2022/0212926 A1 | 7/2022 | Wedhaya et al. |
| 2022/0212927 A1 | 7/2022 | Bamagain et al. |
| 2022/0212928 A1 | 7/2022 | Østberg et al. |
| 2022/0212949 A1 | 7/2022 | Fadhel et al. |
| 2022/0219975 A1 | 7/2022 | Feinstein |
| 2022/0219978 A1 | 7/2022 | Tewari et al. |
| 2022/0234018 A1 | 7/2022 | Mackic et al. |
| 2022/0259042 A1 | 8/2022 | Ravikumar et al. |
| 2022/0267147 A1 | 8/2022 | Ravikumar et al. |
| 2022/0306463 A1 | 9/2022 | Cruz et al. |
| 2022/0306464 A1 | 9/2022 | Cruz et al. |
| 2022/0306468 A1 | 9/2022 | Cady et al. |
| 2022/0331768 A1 | 10/2022 | Ko |
| 2023/0002224 A1 | 1/2023 | Younes et al. |
| 2023/0042457 A1 | 2/2023 | Allam et al. |
| 2023/0061332 A1 | 3/2023 | Stroffolino, IV |
| 2023/0089656 A1 | 3/2023 | Galliot et al. |
| 2023/0104475 A1 | 4/2023 | Nam et al. |
| 2023/0105183 A1 | 4/2023 | Nam et al. |
| 2023/0107936 A1 | 4/2023 | You et al. |

FOREIGN PATENT DOCUMENTS

| | | |
|---|---|---|
| KR | 2011-0133782 | 12/2011 |
| WO | WO 2009/105305 | 8/2009 |
| WO | WO 2012/123752 | 9/2012 |
| WO | WO 2021/055185 | 3/2021 |
| WO | WO 2021/055186 | 3/2021 |
| WO | WO 2021/075802 | 4/2021 |
| WO | WO 2021/083776 | 5/2021 |
| WO | WO 2021/117875 | 6/2021 |
| WO | WO 2021/175662 | 9/2021 |
| WO | WO 2021/189137 | 9/2021 |
| WO | WO 2021/223733 | 11/2021 |
| WO | WO 2021/257944 | 12/2021 |
| WO | WO 2022/003313 | 1/2022 |
| WO | WO 2022/034283 | 2/2022 |
| WO | WO 2022/034284 | 2/2022 |
| WO | WO 2022/034285 | 2/2022 |
| WO | WO 2022/038090 | 2/2022 |
| WO | WO 2022/040677 | 2/2022 |
| WO | WO 2022/100899 | 5/2022 |
| WO | WO 2022/106058 | 5/2022 |
| WO | WO 2022/145618 | 7/2022 |
| WO | WO 2022/173263 | 8/2022 |
| WO | WO 2022/180740 | 9/2022 |
| WO | WO 2022/219822 | 10/2022 |
| WO | WO 2022/229838 | 11/2022 |
| WO | WO 2022/241593 | 11/2022 |
| WO | WO 2022/253460 | 12/2022 |

\* cited by examiner

SYSTEMS AND METHODS FOR POWER PRODUCTION WITH INTEGRATED PRODUCTION OF HYDROGEN

CROSS-REFERENCE TO RELATED APPLICATIONS

The present application is a continuation of U.S. patent application Ser. No. 15/807,803, filed Nov. 9, 2017, which claims priority to U.S. Provisional Patent Application No. 62/419,552, filed Nov. 9, 2016, the disclosures of which are incorporated herein by reference in their entireties.

FIELD OF THE INVENTION

The present disclosure provides power production systems and methods wherein a power production cycle utilizing a $CO_2$ circulating fluid can be configured for simultaneous production of hydrogen.

BACKGROUND

Hydrogen, such as for use in fuel cells, has long been viewed as a desirable energy source because of its clean conversion to and from a source of stored energy. For example, hydrogen can be used as a fuel for electric vehicle propulsion using fuel cells advantageously coupled to high capacity electric storage batteries. Beneficially, use of hydrogen as a fuel can eliminate $CO_2$, NOx, CO, and hydrocarbon emissions and thus significantly reduce air pollution. Any path to implementation of a hydrogen-based world economy, however, would require a very large hydrogen production capacity. Moreover, such hydrogen production method would need to be capable of achieving simultaneously low hydrogen production cost together with the capture of near 100% of the $CO_2$ derived from the fossil fuel utilized.

Hydrogen use as a fuel source can also be beneficial to reduce or eliminate carbon dioxide emissions associated with more conventional power production processes. For example, hydrogen can be diluted with nitrogen and/or steam and used as the fuel in a gas turbine combined cycle power generation system.

Gas turbine combined cycle power generation systems are a major source of electrical power generation worldwide in light of their ability to produce power from natural gas with an efficiency in the range of 60%, on a lower heating value (LHV) basis. Despite the desirable efficiency, such systems are still problematic since the carbon in the fuel is emitted to the atmosphere as carbon dioxide. To overcome this problem, it is possible to operate the gas turbine with $CO_2$ in place of air as the working fluid by recycling the turbine exhaust $CO_2$ gas following cooling and product $CO_2$ removal to the inlet of the gas turbine compressor section. This, too, is problematic because the fuel must be combusted in pure oxygen to produce only $CO_2$ and water as combustion product, and this requires the addition of an air separation plant, which functions as a drain on process efficiency. Chemical and/or physical solvent scrubbing processes are often used to treat the gas turbine exhaust to remove $CO_2$; however, such processes can provide mixed results and again reduce process efficiency due to the added costs of the exhaust treatment systems and upkeep. As discussed above, it is possible to eliminate carbon emissions by utilizing hydrogen as the fuel in the gas turbine; however, such approach requires a consistent hydrogen source that is preferentially provided without associated $CO_2$ production.

Because of the desirability of the use of hydrogen as a fuel source, there remains a need for means to provide hydrogen fuel at a low cost substantially without $CO_2$ emission to the atmosphere.

SUMMARY OF THE INVENTION

The present disclosure relates to systems and methods that combine power production and hydrogen production. In particular, power production (e.g., electrical power) and hydrogen production can be simultaneously achieved with combustion of a hydrocarbon fuel. More particularly, a hydrocarbon fuel can be combusted to provide combustion products that include and/or are converted into hydrogen. Moreover, the hydrogen can be produced with substantially zero carbon emissions, and the hydrogen can be utilized as a fuel for power production.

In some embodiments, the present disclosure further can relate to systems and methods for generation of hydrogen ($H_2$) and carbon monoxide (CO) utilizing oxygen for partial oxidation of a hydrocarbon fuel in a catalytic and/or non-catalytic reaction. For example, a partial oxidation, non-catalytic reactor (PDX) or a catalytic auto-thermal reactor (ATR) can be used. Partial oxidation of the hydrocarbon fuel can be followed by the use of a gas heated reformer (GHR) in either a series or parallel mode to the PDX or ATR reactor to produce additional $H_2$ and CO (i.e., synthesis gas) by utilizing the exhaust sensible heat in the PDX and/or ATR reactor system to provide the heat for endothermic catalytic steam plus natural gas reforming reactions taking place in the GHR.

In one or more embodiments, the present systems and methods can utilize the excess heat generated in the hydrogen plant (e.g., at a temperature level below 400° C.) to provide additional heat input to the power production system and method. Such added heat can be beneficial to assist in achieving high electrical generation efficiency.

In other embodiments, the present disclosure encompasses the provision of heat required for superheating one or both of a fuel stream (e.g., natural gas) and a steam feed stream to an $H_2$+CO synthesis gas generation reactor. This can be achieved, for example, using heat derived from the turbine discharge stream from the power production system and method.

In further embodiments, the present systems and methods can utilize a pressure swing adsorption (PSA) system to separate pure high pressure hydrogen from a cooled, crude hydrogen stream. This can be implemented, for example, following the conversion of CO to $H_2$ by catalytic shift reaction with steam.

In additional embodiments, the present disclosure can provide for the recovery of substantially all the carbon present in the fuel for the hydrogen plant. For example, this can be achieved by compressing the waste gas from the PSA and using it as part of the fuel gas for the power production cycle system and method where the $CO_2$ is recovered from the cooled turbine exhaust stream.

If desired, part or all of the oxygen used in the power production cycle system and method can be supplied from a cryogenic air separation plant or from an oxygen ion transport membrane (ITM) oxy-fuel combustor with a low-pressure air feed. The hydrogen plant can utilize a stream of high pressure gaseous oxygen at pressures up to 105 bar as feed to the PDX and/or ATR producing substantially pure $H_2$ at up to 95 bar from the PSA. A cryogenic air separation plant supplying high pressure oxygen can be particularly useful to provide the oxygen.

Further, if desired, a second fuel oxygen combustor can be used to heat the gas turbine exhaust to provide preheat for any one or more of the $H_2$ plant fuel, oxygen, and steam feed streams. It can be supplied with a gaseous oxygen stream at turbine discharge pressure, but this preferentially can be diluted with $CO_2$ in the $O_2$ burner injection system to control the adiabatic flame temperature. A second alternative is to use an ITM combustor fed with preheated low-pressure air to preheat the turbine exhaust using a preheated natural gas stream blended with the gas turbine exhaust which will burn with the diffusing oxygen and provide the necessary superheating for the natural gas stream and steam feed stream for the synthesis gas reactor.

In one or more embodiments, the present disclosure can provide a power production system or unit that can be configured for simultaneous power production and hydrogen production. In particular, the system can comprise: a combustor; a turbine; a recuperative heat exchanger; a water separator; a compressor; and an integrated hydrogen production system or unit.

In one or more embodiments, the present disclosure can provide a method for power production. In particular, the method can comprise the following:

combusting a carbonaceous fuel in a first combustor with an oxidant in the presence of a recycled $CO_2$ stream at a combustion pressure to provide a combustion product stream including $CO_2$;

expanding the combustion product stream across a turbine to produce power and form a turbine discharge stream including $CO_2$;

cooling the turbine discharge stream including $CO_2$, in a recuperative heat exchanger;

separating $CO_2$ from any further components of the turbine discharge stream to provide a recycled $CO_2$ stream;

compressing the recycled $CO_2$ stream to substantially the combustion pressure;

removing from the recycled $CO_2$ stream the $CO_2$ derived from combustion of carbon in the hydrocarbon or carbonaceous fuel;

heating the compressed recycled $CO_2$ stream in the recuperative heat exchanger, with heat withdrawn from the turbine exhaust stream and/or with external heat supplied at a temperature level below about 400° C.;

passing an optionally preheated carbonaceous fuel (and optionally oxygen and/or steam) through a PDX or ATR optionally followed by a GHR to form a synthesis gas stream that particularly can comprise $H_2$ and CO;

cooling the synthesis gas to generate high pressure steam;

passing the synthesis gas through one or more catalytic shift reactors effective to convert CO and $H_2O$ to $H_2$ and $CO_2$;

separating $H_2$ from the synthesis gas stream; and passing the remaining fuel gas following $H_2$ separation from the synthesis gas stream to one or both of the first combustor and the second combustor.

In the foregoing method, it is understood that not all of the recited steps must be carried in every possible embodiment. Rather, one or more of the above steps can be optional, and a person of skill in the art with knowledge of the present disclosure would be able to recognize the various possible combinations of the steps that can be carried out in separate embodiments.

Further to the foregoing, the presently disclosed systems and method can be further defined in relation to additional elements and configurations. For example, any one or more of the following can apply.

Hydrogen production may specifically be carried out using at least two reactors, such as a partial oxidation reactor and a gas heated reformer reactor.

High temperature heating of a hydrocarbon feed stream and/or a steam feed stream for use in synthesis gas production can utilize heat derived from the power production cycle. In particular, the heat can be derived from at least part of the power production cycle turbine exhaust.

The hydrogen can be separated from one or more waste components in a multi-bed pressure swing absorption unit.

One or more waste components separated from the hydrogen can be compressed and used as part of the fuel in the power production cycle.

Substantially all carbon derived from the hydrocarbon fuel used as the fuel feed in the hydrogen production system and method can be recovered as high pressure $CO_2$ stream, which can be suited for introduction into a $CO_2$ pipeline.

Substantially all low temperature heat (i.e., heat at a temperature above ambient but at a temperature of about 400° C. or less) that is rejected from the $H_2$ plant can be recovered for heat input into the power production cycle.

In one or more embodiments, the present disclosure can provide for the integration of hydrogen production from a fuel (for example, from natural gas), the capture of substantially all of the $CO_2$ derived from carbon in the fuel, and the efficient integration of heat between a power system and the hydrogen production. Preferably, such integration can achieve the production of electrical power from the fuel at a high efficiency (e.g., >60% LHV) with near zero emission of $CO_2$ to the atmosphere and with a cost of electricity substantially similar to the cost arising from current processes that do not provide for partial or complete $CO_2$ capture.

In some embodiments, the present disclosure can provide a system for power production, the system comprising: a power production unit configured for continuous compression, heating, expansion, cooling, and recycling of a $CO_2$ working fluid with no atmospheric exhaust of $CO_2$; a hydrogen production system or unit including a partial oxidation combustor configured to form synthesis gas stream and a separator configured to separate $H_2$ from the synthesis gas stream; and a gas turbine combined cycle unit configured to receive and combust the $H_2$ from the hydrogen production system or unit.

In some embodiments, the present disclosure relates to a power production process and integrated $H_2$ production process comprising:

combusting a gaseous fuel in a combustor with substantially pure O2 at an elevated pressure in the presence of recycled, heated $CO_2$ to form a combustion product stream;

expanding the combustion product stream in a turbine to a lower pressure to produce shaft power and form a turbine exhaust stream;

cooling the turbine exhaust stream in a recuperative heat exchanger to form a cooled turbine exhaust stream while heating a recycled $CO_2$ stream to form the recycled, heated $CO_2$;

optionally adding heat at a temperature level below about 400° C. from an external source into the recycled $CO_2$ stream;

separating condensed water from the cooled turbine exhaust stream to provide the recycled $CO_2$ stream; and compressing the recycled $CO_2$ stream to a pressure suitable for input to the combustor;

wherein one or more of the following conditions apply:

one or both of a hydrocarbon or carbonaceous fuel stream and a steam stream that is fed to an $H_2$ synthesis plant reactor is heated utilizing heat transferred from the turbine exhaust stream;

the turbine combustor fuel inlet flow and the turbine inlet temperature are increased to provide additional power from the turbine plus the heat required for the preheating of hydrocarbon or carbonaceous and steam feeds to the $H_2$ plant synthesis reactors and with substantially the same turbine inlet temperature to the recuperative heat exchanger as in a stand-alone $CO_2$ power cycle;

excess heat from the $H_2$ synthesis plant at a temperature level below about 400° C. is transferred from the $H_2$ synthesis plant to the recycled $CO_2$ stream;

hydrogen is separated from a total impure $H_2$ product stream in the $H_2$ synthesis plant following CO conversion to $H_2$ in one or more CO catalytic shift reactors, followed by cooling to near ambient temperature and liquid water removal;

a waste fuel gas remaining after $H_2$ separation in the $H_2$ synthesis plant is compressed to a pressure suitable for input to the combustor;

$H_2$ separation in the $H_2$ synthesis plant is carried out in a plurality of stages;

$H_2$ separation in the $H_2$ synthesis plant includes intermediate $CO_2$ removal and catalytic CO shift conversion to $H_2$;

a second combustor is utilized, the second combustor using substantially pure oxygen and a fuel gas plus at least part of the turbine exhaust to provide at least part of the heat required for preheating hydrocarbon or carbonaceous and steam feeds to the $H_2$ plant synthesis reactors;

a heated, pressurized water and/or steam stream at a temperature below about 400° C. is provided and carries excess heat from the $H_2$ synthesis plant to the recycled $CO_2$ stream;

produced $H_2$ from the $H_2$ synthesis plant is combined with $N_2$ and/or steam to produce a fuel gas suitable for combustion in a gas turbine to produce power.

In one or more embodiments, the present disclosure can particularly provide a system for combined power production and hydrogen production, the system comprising: a power production unit wherein pressurized carbon dioxide is expanded for power production; a hydrogen production unit wherein a hydrocarbon fuel is partially oxidized to produce a synthesis gas from which hydrogen is separated; and one or more flow components configured for passage of one or more streams between the power production unit and the hydrogen production unit.

In further embodiments, the noted system for combined power production and hydrogen production can be further defined in relation to any one or more of the following statements, which can be combined in any order and number.

The power production unit can comprise: a combustor configured to receive a hydrocarbon fuel and oxygen and output a heated stream comprising at least the pressurized carbon dioxide; a turbine configured to receive and expand the heated stream comprising the pressurized carbon dioxide from the combustor to produce the power and form a heated stream comprising the expanded carbon dioxide; a recuperative heat exchanger configured to receive the heated stream comprising the expanded carbon dioxide and form a cooled stream comprising carbon dioxide; a separator configured to receive the cooled stream comprising the carbon dioxide from the recuperative heat exchanger and provide a stream of the carbon dioxide; and a compressor configured to receive the stream of the carbon dioxide from the separator and compress the carbon dioxide.

The hydrogen production unit can comprise: a partial oxidation combustor configured to receive oxygen and a portion of the hydrocarbon fuel and output the synthesis gas; a reformer in fluid communication with the partial oxidation combustor and configured to receive the synthesis gas from the partial oxidation combustor and to receive a portion of the hydrocarbon fuel; a shift reactor in fluid communication with the reformer; a shift stream heat exchanger in fluid communication with the shift reactor; a separator in fluid communication with the shift stream heat exchanger; and a pressure swing adsorption unit in fluid communication with the separator; wherein the pressure swing adsorption unit is configured to output a stream of substantially pure hydrogen.

The hydrocarbon fuel can be provided to the partial oxidation combustor and the reformer from a hydrocarbon fuel line that passes through the shift stream heat exchanger.

The hydrocarbon fuel line can pass through a supplemental heat exchanger that is configured to receive and cool the heated stream comprising the expanded carbon dioxide exiting the turbine of the power production unit.

The system can further comprise a water line that can be configured for passing water to the reformer.

The water line can pass through the shift stream heat exchanger.

The water line can pass through a supplemental heat exchanger that is configured to receive and cool the heated stream comprising the expanded carbon dioxide exiting the turbine of the power production unit.

The pressure swing adsorption unit can be configured to output a waste stream that is separated from the stream of substantially pure hydrogen, wherein the waste stream comprises one or more or carbon monoxide, carbon dioxide, hydrogen, methane, argon, and nitrogen.

One or more flow components configured for passage of one or more streams between the power production unit and the hydrogen production unit can include a line for passage of at least a portion of the waste stream from the pressure swing adsorption unit to the combustor of the power production unit.

The power production unit can further comprise an additive heat exchanger configured to heat a stream of substantially pure carbon dioxide against one or more compressed streams from the power production unit.

The additive heat exchanger can be further configured to heat the stream of substantially pure carbon dioxide against a stream from the hydrogen production unit.

In one or more embodiments, the present disclosure particularly can provide a method for combined power production and hydrogen production, the method comprising: carrying out power production in a power production unit comprising: combusting a first hydrocarbon fuel in a first combustor with an oxidant in the presence of a recycled $CO_2$ stream at a combustion pressure to provide a combustion product stream including $CO_2$; expanding the combustion product stream including $CO_2$ across a turbine to produce power and form a turbine discharge stream including $CO_2$; cooling the turbine discharge stream including $CO_2$, in a recuperative heat exchanger; separating $CO_2$ from any further components of the turbine discharge stream to provide a stream comprising the recycled $CO_2$; compressing the stream comprising the recycled $CO_2$ to substantially the combustion pressure; heating the compressed recycled $CO_2$ stream in the recuperative heat exchanger, with heat withdrawn from the turbine exhaust stream to provide a heated stream comprising the recycled $CO_2$; and passing the heated stream comprising the recycled $CO_2$ to the first combustor; and carrying out hydrogen production in a hydrogen production unit comprising: passing a stream of a second hydrocarbon fuel through a partial oxidation reactor to form a synthesis gas stream; and processing the synthesis gas to provide a stream of substantially pure hydrogen and a waste stream comprising at least carbon monoxide.

In further embodiments, the noted method for combined power production and hydrogen production can be further defined in relation to any one or more of the following statements, which can be combined in any order and number The method can further comprise passing at least the carbon monoxide from the waste stream to the first combustor.

The processing of the synthesis gas can comprise passing the synthesis gas through a reformer that is also configured to receive a stream of the second hydrocarbon fuel gas and a stream of heated water.

One or more of the stream of the second hydrocarbon fuel passing through the partial oxidation reactor, the stream of the second hydrocarbon fuel received by the reformer, and the stream of the heated water that is received by the reformed can be heated in a supplemental heat exchanger utilizing heat transferred from the turbine discharge stream including $CO_2$.

Processing the synthesis gas can comprise passing reformed synthesis gas from the reformer through a shift reactor followed by a shift stream heat exchanger.

The stream of the hydrocarbon fuel can be provided to one or both of the partial oxidation combustor and the reformer via a hydrocarbon fuel line that passes through the shift stream heat exchanger.

The stream of heated water received in the reformer can be provided through a water line that passes through the shift stream heat exchanger.

The method can further comprise passing a stream exiting the shift stream heat exchanger through a water separator to remove water and form a crude hydrogen stream including hydrogen and impurities.

The method can further comprise passing the crude hydrogen stream through a pressure swing adsorption unit that outputs the substantially pure hydrogen and the waste stream.

The waste stream can be compressed to a pressure suitable for input to the combustor of the power production unit and then passed to the combustor of the power production unit.

The power production unit can further comprise an additive heat exchanger that heats a stream of the recycled $CO_2$ against one or more compressed streams from the power production unit.

The method can further comprise passing a heated stream from the hydrogen production unit through the additive heat exchanger such that heat from the hydrogen production unit is transferred to the stream of the recycled $CO_2$.

The heat that is transferred from the hydrogen production unit to the stream of the recycled $CO_2$ can be at a temperature level below about 400° C.

At least a portion of the turbine discharge stream including $CO_2$ can be passed through a second combustor with a stream of the first hydrocarbon fuel and oxygen so that the first hydrocarbon fuel is combusted to provide additional heat to at least a portion of the turbine discharge stream including $CO_2$.

At least part of the additional heat provided to at least a portion of the turbine discharge stream including $CO_2$ can be provided to one or more streams in the hydrogen production unit.

The method can further comprise carrying out power production in a gas turbine that is separate from the power production unit wherein at least a portion of the substantially pure hydrogen is combusted in the gas turbine to produce power.

In one or more embodiments, the present disclosure further can provide a system for power production, the system comprising: a power production unit configured for continuous compression, heating, expansion, cooling, and recycling of a $CO_2$ working fluid with no atmospheric exhaust of $CO_2$; a hydrogen production unit including a partial oxidation combustor configured to form a synthesis gas stream and one or more additional components configured to process the synthesis gas to form a stream a substantially pure hydrogen and a waste stream; and a gas turbine combined cycle unit configured to receive and combust at least a portion of the substantially pure hydrogen from the hydrogen production unit.

BRIEF DESCRIPTION OF THE DRAWINGS

Figure 1:
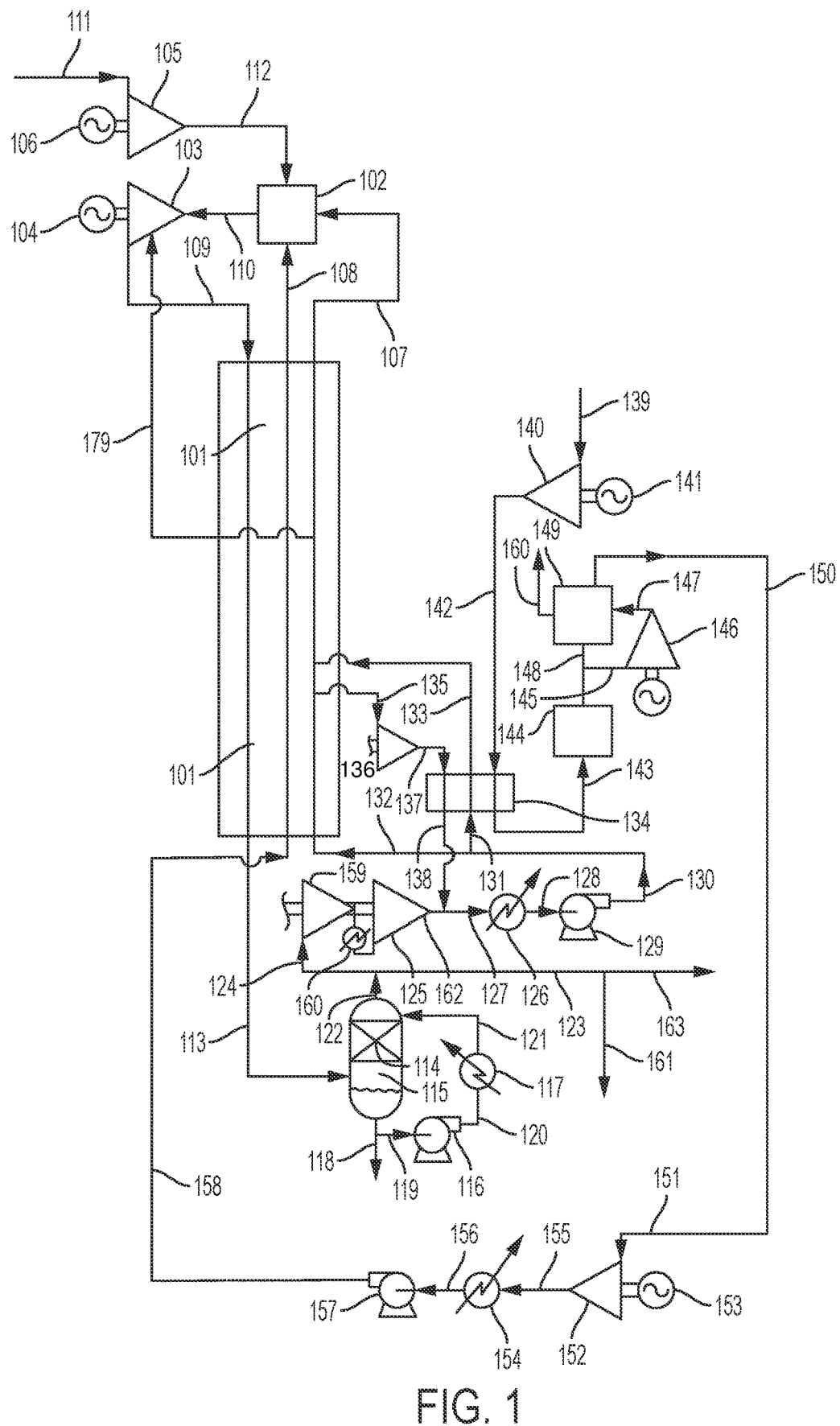
Figure 2:
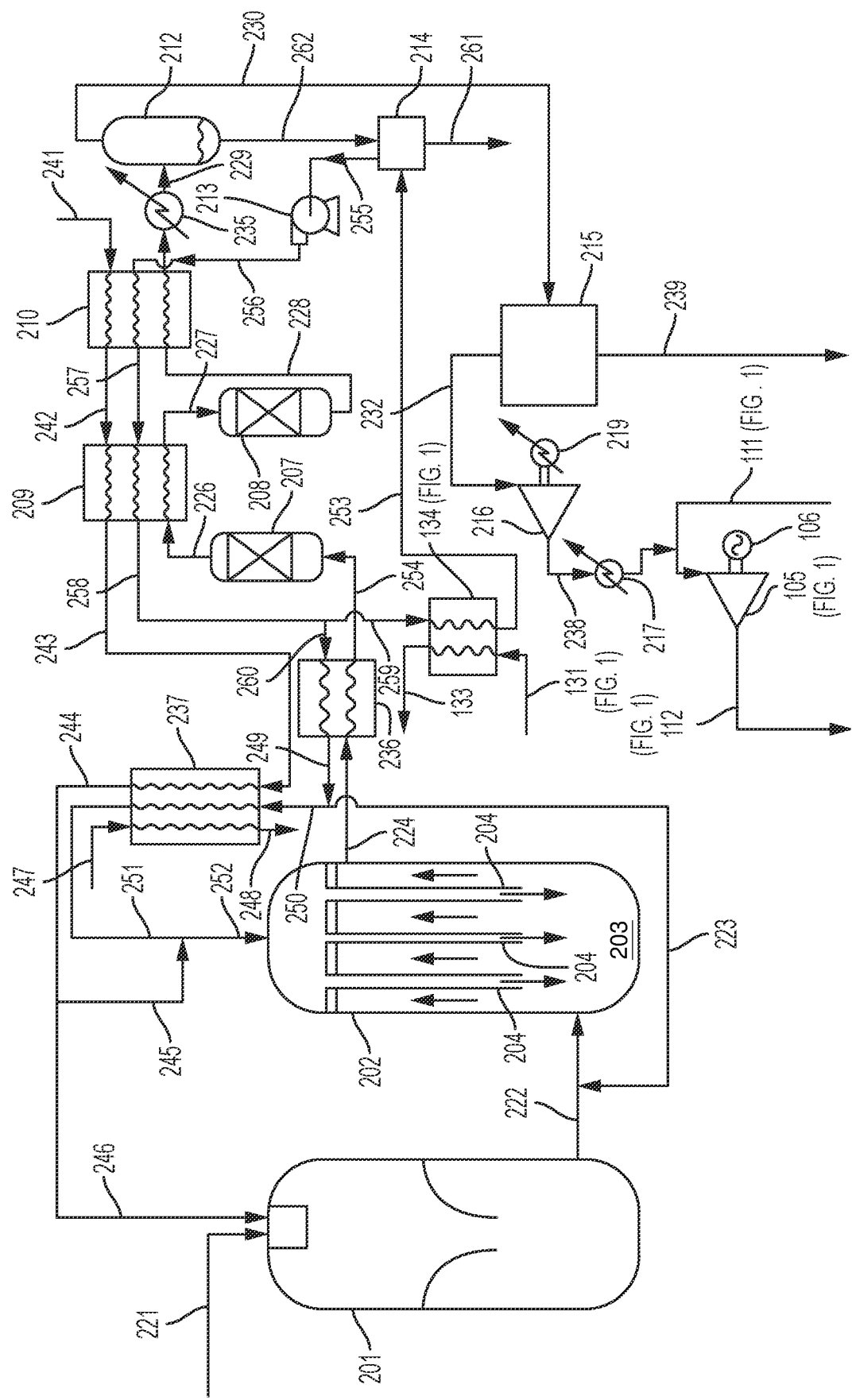
Figure 3:
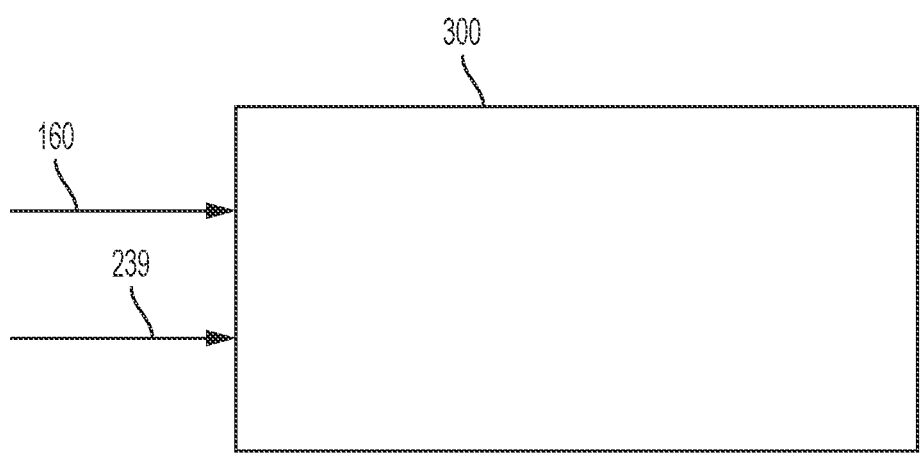

Having thus described the disclosure in the foregoing general terms, reference will now be made to the accompanying drawings, which are not necessarily drawn to scale, and wherein:

FIG. 1 is a flow diagram of an exemplary system and method of power production using a $CO_2$ working fluid and including a cryogenic oxygen plant;

FIG. 2 is a flow diagram of a hydrogen production facility including elements for integration with a power production system and method, such as illustrated in FIG. 1; and FIG. 3 is a flow diagram illustrating a combined system wherein nitrogen gas from the air separation unit and hydrogen gas from the hydrogen generation unit are input to a gas turbine combined cycle unit.

DETAILED DESCRIPTION

The present subject matter will now be described more fully hereinafter with reference to exemplary embodiments thereof. These exemplary embodiments are described so that this disclosure will be thorough and complete, and will fully convey the scope of the subject matter to those skilled in the art. Indeed, the subject matter can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides systems and methods wherein power production and hydrogen production are simultaneously achieved. Previous efforts have been undertaken to provide for simultaneous production of power and hydrogen, and one or more elements from such previous endeavors may be integrated into the presently disclosed systems and methods. For example, U.S. Pat. No. 6,534,551 to Allam et al. describes the combination of: 1) a hydrocarbon fuel gas reaction with steam and or oxygen; and 2) a power system utilizing a compressed oxidant gas in which a fuel gas is burned with combustor products producing power by work expansion and in which the expanded combustion product gas is used to superheat the steam used in hydrogen synthesis reactions and in which the oxygen production unit is driven by at least a portion of the power produced by the expansion of the combustion product gas. The disclosure of U.S. Pat. No. 6,534,551 to Allam et al. is incorporated herein by reference.

In one or more embodiments, the present systems and methods can beneficially provide for hydrogen production in combination with power production with capture of substantially all of the carbon produced, particularly substantially all of the $CO_2$ produced. The combination can be a single system with a combination of elements suitable to achieve the simultaneous production of hydrogen and power. In some embodiments, a hydrogen production system or unit can be operated in parallel with a power production system or unit with the appropriate crossover of elements so that the two systems or units are functioning as a single, integrated system. In this manner, the present disclosure may refer to a hydrogen plant, and it is understood that such hydrogen plant refers to the combination of elements necessary to form the hydrogen production system or unit utilized herein.

A power production cycle useful according to the present disclosure can include any system and method wherein $CO_2$ (particularly supercritical $CO_2$— or $sCO_2$) is used in a work stream. As a non-limiting example, U.S. Pat. No. 8,596,075 to Allam et al., which is incorporated herein by reference, describes a system and method wherein a recycle $CO_2$ stream is directly heated and used in power production. Specifically, the recycle $CO_2$ stream is provided at high temperature and high pressure, is provided to a combustor wherein a carbonaceous fuel is combusted in oxygen, is expanded across a turbine to produce power, is cooled in a heat exchanger, is purified to remove water and any other impurities, is pressurized, is re-heated using the heat taken from the turbine exhaust, and is again passed to the combustor to repeat the cycle. Such system and method are beneficial in that all fuel and combustion derived impurities, excess $CO_2$, and water are removed as a gaseous or supercritical fluid, a liquid or a solid (e.g., ash), and there is virtually zero atmospheric emission of any streams. The system and method achieves high efficiency through, for example, the use of low temperature level (i.e., less than 500° C.) heat input after the recycle $CO_2$ stream has been re-pressurized and before combustion (i.e., low temperature level heat added to the recycle $CO_2$ stream in addition to the recuperated heat from the turbine exhaust stream). It is understood that reference to a power production cycle herein indicates a power production cycle utilizing a $CO_2$ working fluid and the combination of elements and method steps described herein and in the incorporated documents.

A power production cycle useful according to the present disclosure can include more steps or fewer steps than described above and can generally include any cycle wherein a high pressure recycle $CO_2$ stream is expanded for power production and recycled again for further power production. As used herein, a high pressure recycle $CO_2$ stream can have a pressure of at least 100 bar (10 MPa), at least 200 bar (20 MPa), or at least 300 bar (30 MPa). In all instances, the upper limit on pressure may be dictated by the limits of the available equipment at the time of implementation of a system and/or method according to the present disclosure. A high pressure recycle $CO_2$ stream can, in some embodiments, have a pressure of about 100 bar (10 MPa) to about 500 bar (50 MPa), about 150 bar to about 450 bar (45 MPa), or about 200 bar (20 MPa) to about 400 bar (40 MPa). Reference to a high pressure recycle $CO_2$ stream herein may thus be a $CO_2$ stream at a pressure within the foregoing ranges. Such pressures also apply to references to other high pressure streams described herein, such as a high pressure work stream comprising $CO_2$. Combustion may be carried out at a temperature of about 400° C. or greater, about 500° C. or greater, about 600° C. or greater, about 800° C. or greater, or about 1000° C. or greater. In all instances, the upper limit on temperature may be dictated by the limits of the available equipment at the time of implementation of a system and/or method according to the present disclosure. In some embodiments, the first combustor outlet temperature following mixing with recycle $CO_2$ can be about 400° C. to about 1,500° C., about 500° C. to about 1200° C., or about 600° C. to about 1000° C.

In some embodiments, integration of a power production cycle as described above with a hydrogen production facility can utilize the excess low temperature level heat produced by the hydrogen plant in order to increase the efficiency of power production. For example, superheating of the steam and hydrocarbon feed in the turbine exhaust stream can be carried out with an increase in turbine power output in the power production system and method. Further, the hydrogen plant can be integrated with the power production cycle so that substantially all of the $CO_2$ derived from carbon present in the hydrocarbon fuel feed into the hydrogen plant or system is captured and, optionally, combined with the $CO_2$ captured from the power production cycle plant or system. The integrated system captures up to 100% of the $CO_2$ produced from both the power and $H_2$ plants with zero emission to the atmosphere.

A hydrogen production plant for use according to the present disclosure can incorporate any variety of elements known to be suitable in prior hydrogen production plants. For example, a hydrogen production plant can comprises a two stage reactor system including a first stage reactor which converts a hydrocarbon feed to a $CO+H_2$ gas using partial oxidation of the hydrocarbon with oxygen and optionally with the additional use of steam. In some embodiments, such partial oxidation (PDX) of a natural gas feed with pure oxygen can be carried out at an outlet temperature of about 1300° C. to about 1500° C. at typical pressures of about 30 bar to about 150 bar. An auto-thermal reformer (ATR) can add steam and excess hydrocarbon, generally natural gas, after the partial oxidation burner so that the high temperature gases can then pass through a bed of catalyst where subsequent steam-hydrocarbon reforming reactions take place yielding further $H_2+CO$ and cooling the gas mixture to an outlet temperature of about 1000° C. to about 1100° C. at pressures of about 30 bar to about 150 bar. The second stage reactor can comprise a steam/hydrocarbon catalytic reformer in which the total $H_2+CO$ gas product from both reactors (e.g., at a temperature of about 1000° C. or greater) is used to provide the endothermic heat of the reforming reactions in a convectively heated shell side flow with catalyst in the tubes. Optionally the two reactors can operate in a series or parallel mode. A favorable configuration uses a vertical gas heated reformer (GHR) with catalyst filled open ended tubes hanging from a single tube sheet at the top of the vessel, with the product $H_2+CO$ leaving the reformer tubes and mixing with the product gas from a PDX reactor or an ATR in the base of the GHR, and the total product $H_2+CO$ stream passing through the shell side and cooling typically from about 1050° C. to 550° C. to 800° C.

An advantage of the two reactor configuration is that the yield of $H_2+CO$ from hydrocarbon feed is maximized, and all $CO_2$ formed in the reactions is contained within the high-pressure system. The product $CO+H_2$ gas is further cooled in a steam generating waste heat boiler (WHB), and a further advantage is that this steam quantity is only sufficient to provide the required steam flow to the two $H_2$+CO reactors with only a small excess flow. The system has no large by-product steam production.

To generate hydrogen, the $H_2$+CO product leaving the WHB at a typical temperature of about 240° C. to about 290° C. and containing typically about 20% to about 40% (molar) steam is passed through one or more catalytic shift converters where CO reacts with steam to produce $CO_2$ and additional $H_2$. The reactions for the whole $H_2$ production process sequence are shown below (using $CH_4$ as the hydrocarbon)

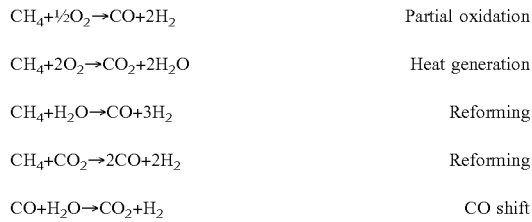

| | |
|---|---|
| $CH_4 + \tfrac{1}{2}O_2 \rightarrow CO + 2H_2$ | Partial oxidation |
| $CH_4 + 2O_2 \rightarrow CO_2 + 2H_2O$ | Heat generation |
| $CH_4 + H_2O \rightarrow CO + 3H_2$ | Reforming |
| $CH_4 + CO_2 \rightarrow 2CO + 2H_2$ | Reforming |
| $CO + H_2O \rightarrow CO_2 + H_2$ | CO shift |

The total CO+$H_2$ product passing through the CO shift reactors is cooled, and a significant amount of heat is released generally at a temperature level of about 290° C. or lower as the gas cools and steam condenses. This heat is released not at a single temperature level but over a temperature range down to near ambient temperature. Part of this heat release can be used to preheat boiler feed water, but there is a large excess quantity that is at a low temperature level and only available over a temperature range.

The efficiency of the $H_2$+CO generation in the two reactors can be significantly increased by preheating the hydrocarbon and steam feeds to typically about 400° C. to about 550° C. and preferably to about 500° C. to about 550° C. This preferably is done using an external heat source since no excess heat at these temperature levels is available within the $H_2$+CO generation reactors plus WHB.

The cooled $H_2$ rich gas stream is next passed through a cooler (e.g., an ambient cooler) where condensed water is removed. The gas stream is then passed to a separator wherein substantially pure hydrogen can be isolated. For example, the gas stream can be passed through a conventional multi-bed pressure swing adsorber which separates typically about 85% to about 90% (molar) of the hydrogen as a pure stream having typically about 10 ppm to about 50 ppm total impurities and having a drop in pressure from feed to product $H_2$ of typically about 1 bar to about 2 bar. All the impurities in the crude $H_2$ feed stream are separated as a waste fuel gas stream, which waste stream can comprise any combination of components, such as $H_2$, CO, $CO_2$, $CH_4$, $N_2$, argon, and a small quantity of vapor phase $H_2O$. The pressure is typically about 1.1 bar to about 1.5 bar. This waste gas typically has about 20% of the total hydrocarbon reactor hydrocarbon feed lower heating value (LHV) so its efficient use is advantageous to the overall economics of $H_2$ production. The waste gas contains all the carbon from the total hydrocarbon feed as $CO_2$+CO and the recovery of this carbon as pure $CO_2$ at pipeline high pressure is likewise advantageous to meet climate change emission objectives.

The integration of the high-pressure, two-reactor hydrogen generation system with power production cycle utilizing a $CO_2$ working stream can achieve a variety of benefits. The turbine exhaust from the power production cycle is typically in the range of about 700° C. to about 800° C. The steam and hydrocarbon feeds to the two reactors can be preheated to a range of about 500° C. to about 550° C. utilizing part of the turbine exhaust flow in a separate heat exchanger. This simply requires an increase in the fuel burned in the turbine combustor to provide the extra heat required. This increases the turbine inlet temperature and flow rate and provides a significant additional power output from the turbine. The steam and hydrocarbon or carbonaceous fuel can be heated to a typical temperature of about 400° C. to about 550° C. while the turbine exhaust can be cooled to a typical temperature of about 700° C. to about 800° C. before entering the recuperative heat exchanger.

As an alternative arrangement, a second combustor can be provided to preheat at least part of the turbine exhaust stream to deliver the heat required for preheating the fuel and steam required for the generation of synthesis gas in the two stage reactor system. One combustor arrangement uses an oxidant comprising substantially pure $O_2$ diluted with $CO_2$ to produce an oxidant containing 20% to 30% molar $O_2$ to burn the fuel. A second combustor arrangement uses an $O_2$ ion transport membrane reactor that diffuses substantially pure $O_2$ derived from a preheated low pressure air stream into at least a portion of the turbine exhaust to which has been added a controlled portion of the fuel so that the temperature is increased as desired for $H_2$ plant preheat duty.

The waste gas from the PSA can be compressed to typically about 200 bar to about 400 bar and mixed with the feed hydrocarbon and used very efficiently as fuel gas in the power production cycle. An additional advantage is that the carbon from the hydrocarbon reactor feeds can be captured as $CO_2$ within the power production cycle system. A further advantage is the large mass flow of the waste gas due to its high CO+$CO_2$ content of typically about 50% to about 70% (molar) that increases extra turbine power. Alternatively the waste gas from the PSA can be compressed to the inlet pressure of the first PSA, the $CO_2$ can be removed in one of a number of known processes, and the $CO_2$ depleted gas stream can be sent to a second PSA to separate more $H_2$ to add to the total $H_2$ product stream. Optionally the waste gas can be preheated in an economizer heat exchanger, steam can be added, and more $H_2$ can be produced in an additional catalytic CO shift reactor. The gas can then be cooled in the economizer heat exchanger before being processed to separate more $H_2$ in the second PSA.

The significant quantity of low grade heat available from the cooling $H_2$+CO stream is ideally suited to provide the low temperature level heat that can be added to the power production cycle to augment the recuperated heat from the turbine exhaust and thus achieve a high efficiency. Specifically, the "low grade" heat from the cooling $H_2$+CO stream can be at a temperature level of about 200° C. to about 400° C., about 220° C. to about 350° C., and particularly about 240° C. to about 290° C. Depending on $H_2$ output, this can result in the power production cycle oxygen plant main air compressor being a conventional inter-cooled compressor rather than an adiabatic unit with significant parasitic power reduction in the power production cycle. It will also lead to lower hot $CO_2$ compressor flow with further parasitic power reductions. The availability of this excess heat over a temperature range as noted above (and down to near ambient) suits the heating of a side-stream of high pressure recycle $CO_2$ over a similar temperature range. The integration system defined is equally applicable to power production cycle systems utilizing conventional cryogenic oxygen production plus an oxy-fuel combustor or to systems utilizing oxygen ion combustors.

Integrated power production and hydrogen production according to the present disclosure is described hereafter in relation the various figures. In particular, FIG. 1 illustrates a power production cycle system having a cryogenic oxygen plant and using a natural gas fuel. Although the system is described below in relation to operating parameters corresponding to an exemplary embodiment, it is understood that the power production cycle can be as defined otherwise herein. Further, the power production cycle can incorporate elements and/or operating parameters as otherwise described in U.S. Pat. No. 9,068,743 to Palmer et al., U.S. Pat. No. 9,062,608 to Allam et al., U.S. Pat. No. 8,986,002 to Palmer et al., U.S. Pat. No. 8,959,887 to Allam et al., U.S. Pat. No. 8,869,889 to Palmer et al., U.S. Pat. No. 8,776,532 to Allam et al., and U.S. Pat. No. 8,596,075 to Allam et al, the disclosures of which are incorporated herein by reference.

In one or more embodiments, a power production cycle according to the present disclosure can be configure such that a working fluid comprising $CO_2$ is repeatedly cycled at least through stages of compressing, heating, expanding, and cooling. The $CO_2$ in particular can be supercritical through at least some of these steps, although it can transition between supercritical and liquid and/or gaseous states in some embodiments. In various embodiments, a power production cycle for which efficiency can be improved may include combinations of the following steps:

- combustion of a carbonaceous fuel with an oxidant in the presence of a recycled $CO_2$ stream to provide a combustion product stream at a temperature of at least about 500° C. or at least about 700° C. (e.g., about 500° C. to about 2000° C. or about 600° C. to about 1500° C.) and a pressure of at least about 100 bar (10 MPa) or at least about 200 bar (20 MPa) (e.g., about 100 bar (10 MPa) to about 500 bar (50 MPa) or about 150 bar (15 MPa) to about 400 bar (40 MPa));
- expansion of a high pressure recycled $CO_2$ stream (e.g., at a pressure as noted above) across a turbine for power production;
- cooling of a high temperature recycled $CO_2$ stream (e.g., at a pressure as noted above), particularly of a turbine discharge stream, in a recuperative heat exchanger;
- condensing of one or more combustion products (e.g., water) in the recuperative heat exchange and in an ambient cooler, the combustion products being present particularly in a combustion product stream that has been expanded and cooled;
- separating water and/or further materials from $CO_2$ to form a recycled $CO_2$ stream;
- compressing a recycled $CO_2$ stream to a high pressure (e.g., a pressure as noted above), optionally being carried out in multiple stages with inter-cooling to increase stream density;
- heating a compressed recycled $CO_2$ stream in a recuperative heat exchanger, particularly heating against a cooling turbine exhaust stream; and
- optionally adding heat to the recycled $CO_2$ stream in addition to the heat recuperated from the cooling turbine exhaust stream, said heat being from another source, such as low grade heat taken from the hydrogen production system or unit as described herein.

Turning more specifically to FIG. 1, a power production unit suitable for combination with a hydrogen production unit is exemplified. It is understood that a power production unit is intended to encompass a combination of individual components that, when operated together, are effective for power production and, as such, is intended to have the same meaning as a power production system. Likewise, it is understood that a hydrogen production unit is intended to encompass a combination of individual components that, when operated together, are effective for hydrogen production and, as such, is intended to have the same meaning as a hydrogen production system. Although the exemplified power production unit is described in relation to specific operating parameters, it is understood that the power production unit can be operated across a range of parameters consistent with the overall disclosure herein. In the power production unit exemplified in FIG. 1, a $CO_2$ stream 107 at 304 bar, heated to 715° C. in heat exchanger 101 enters a combustor 102 where it mixes with the combustion products derived from a methane stream 112 compressed to 305 bar (251° C.) in compressor 105 driven by electric motor 106 burning in an oxidant stream 108 which has a composition of about 25% oxygen and about 75% $CO_2$ molar and has been heated to 715° C. in heat exchanger 101. The resulting mixed stream 110 enters the turbine 103 at 1150° C. and 300 bar and is expanded to 30 bar and 725° C. leaving as stream 109 and generating power in generator 104. The 30 bar stream cools in the heat exchanger 101 and transfers heat to the high pressure $CO_2$ stream and leaves at 65° C. as stream 113. It is further cooled in direct contact water cooler 115 that has a packed section 114 and a circulating water section comprising a pump 116 and an indirect water-cooled heat exchanger 117, which directs water flows 119, 120 and 121 to the top of the packing section. The excess liquid water produced from $CH_4$ combustion, stream 118, is removed from the base of water cooler 115. The cooled stream of substantially pure $CO_2$ 122 leaving the top of the cooler 115 splits into multiple streams. A first portion 123 of the substantially pure $CO_2$ stream 122 is divided into a net $CO_2$ product stream 161, which is drawn off for export or other use and a diluent stream 163. In preferred embodiments, diluent stream 163 blends with the combustor oxygen flow 150 at 29 bar to form the combustor oxidant stream 151 containing 25% (molar) oxygen. The main portion 124 of the cooled, substantially pure $CO_2$ enters a two stage inter-cooled $CO_2$ compressor (with first compressor stage 159, intercooler 160, and second compressor state 125) where it is compressed to 67.5 bar, leaving as stream 162. The $CO_2$ stream exiting the cooler 115 is substantially pure in that it comprises less than 3 mol %, less than 2 mol %, less than 1 mol %, less than 0.5 mol %, less than 0.1 mol %, or less than 0.01 mol % impurities.

The power production cycle requires a significant quantity of additionally generated heat to be provided to the high pressure $CO_2$ stream at a temperature level below 400° C. In this exemplified embodiment, the heat is derived from two sources that provide heat of compression. The first source is the adiabatically compressed cryogenic oxygen plant feed air stream 142 at 5.6 bar and 226° C. from air compressor 140, which compresses air stream 139 driven by electric motor 141. The second source is a stream 135 of 29.3 bar $CO_2$ taken from heat exchanger 101 at a temperature of 135° C. and adiabatically compressed in compressor 136 to produce stream 137 at 226° C. These two streams are passed through additive heat exchanger 134 where they provide additive heat to a 304 bar $CO_2$ stream 131 split from discharge stream 130 that is taken directly from the multistage pump 129. The additive heat from the additive heat exchange 134 raises the temperature of the $CO_2$ from 50° C. in stream 131 to 221° C. in stream 133. The cooled $CO_2$ stream 138 and the $CO_2$ recycle compressor discharge stream 162 combine to form the total $CO_2$ stream 127 that is cooled in the cooling water heat exchanger 126 to produce $CO_2$ recycle stream 128 at 19.7° C. This stream of high-density $CO_2$ liquid is compressed to 305 bar in a multi-stage pump 129. The discharge stream 130 at 50° C. divides into a main portion 132 which enters the recuperative heat exchanger 101 and a minor stream 131 that is heated in heat exchanger 134 to 221° C. against the cooling adiabatically compressed streams 137 and 142 producing stream 133 as noted above. The stream 133 rejoins the main portion 132 of the high pressure $CO_2$ flow in heat exchanger 101. In this manner, additive heating is provided to the recycled $CO_2$ stream (i.e., in addition to the recuperated heat from the turbine discharge stream 109) in order to achieve a high level of operating efficiency. A side stream 179 can be taken from the main portion 132 of the high pressure $CO_2$ stream and directed to the turbine 103 as a turbine blade cooling stream.

The cooled air stream 143 at 56° C. enters the cryogenic air separation system. This comprises an air purification unit 144 that has a direct contact air cooler, a water chiller, and a switching duel bed thermally regenerated adsorption unit that delivers a dry $CO_2$ free stream of air at 5.6 bar and 12° C. Part of this air (stream 145) is compressed to 70 bar in compressor 146 driven by electric motor 178, and air streams 148 and 147 enter a pumped liquid oxygen cycle air separation cryogenic system 149. The products from the air separator are a waste nitrogen stream 160 and a 30 bar product oxygen stream 150, which blends with a cooled portion of the $CO_2$ stream (the diluent stream 163) leaving the direct contact $CO_2$ cooler 115 to produce the oxidant stream 151. This is compressed to 304 bar in the $CO_2/O_2$ compression train. Specifically, the oxidant stream 151 is compressed in compressor 152 driven by electric motor 153 leaving as stream 155, which is cooled in intercooler 154, leaving as stream 156, which is compressed further in pump 157. The resulting compressed oxidant stream 158 is heated to 715° C. in heat exchanger 101 leaving as stream 108 to enter the combustor 102.

The power production cycle requires a separate cryogenic air separator plant to produce oxygen. This must be delivered to the combustor at a controlled concentration of about 20% to about 30% molar preheated to typically over 700° C. diluted with $CO_2$ which in general involves a separate $O_2/CO_2$ compressor train or alternatively a more complex cryogenic air separation plant with a significantly high power consumption. The $CH_4$ fuel 111 is compressed to 305 bar in a high-pressure compressor 105 as discussed above.

The integration of the hydrogen plant with the power production cycle system (fueled with natural gas in the exemplified embodiment) is shown in FIG. 2. The system has a partial oxidation (PDX) reactor 201 with a feed stream 221 of 99.5% pure $O_2$ at 270° C. and a natural gas stream 246 at 500° C., both at 85 bar pressure. The PDX reactor 201 provides a product $H_2+CO$ stream 222 at 1446° C. (which can optionally be quenched and cooled by the addition of a saturated steam stream 223 to 1350° C.) enters the base 203 of the gas heated reformer reactor 202. The product $H_2+CO$ stream 222 mixes with reformed $H_2+CO$ product stream leaving each of the open ended catalyst filled tubes 204, and the total product $CO+H_2$ stream passes upwards through the shell side, providing heat for the endothermic reforming reactions and leaving as stream 224 at 600° C. The tubes are free to expand downwards at operating temperatures and the pressure difference at the hot end and hence stresses in the tube walls are negligible. The tubes plus any exposed metal parts are fabricated from an alloy such as INCONEL® 693, which is resistant to metal dusting corrosion caused by Boudouard reaction depositing carbon. Additionally, the metal surfaces can be further protected by coating with alumina.

Stream 224 is cooled by passage through a waste heat boiler 236 and leaves as product gas stream 254 at 320° C. The product gas stream 254 passes through two catalyst filled CO shift reactors 207 and 208 in series. The outlet streams 226 and 228 enter the shift stream heat recovery heat exchangers 209 and 210 where heat is used for boiler feed-water preheating and natural gas stream preheating. Specifically, stream 226 leaving CO shift reactor 207 passes through shift stream heat exchanger 209 leaving as stream 227 to enter CO shift reactor 208. The stream 228 leaving CO shift reactor 208 passes through shift stream heat exchanger 210 before passing through water cooler 235 to leave as stream 229. Boiler feedwater streams 256 and 257 are heated in shift stream heat exchangers 210 and 209, respectively to provide heated water stream 258. Natural gas streams 241 and 242 are heated in the shift stream heat exchangers 210 and 209, respectively, to provide natural gas stream 243 at 290° C. The boiler feed-water stream 258 divides into a waste heat boiler feed stream 260 and a large excess stream 259 at 290° C. which is cooled to 60° C. in the heat exchanger 134 (see FIG. 1) releasing its heat to a portion of the power production cycle recycle high pressure $CO_2$ stream 131 to 133 (shown in FIG. 1).

The crude $H_2$ stream 271 leaving heat exchanger 210 (which contains substantially all of the $CO_2$ derived from combustion of carbon in the hydrocarbon or carbonaceous feed together with water vapor and minor amounts of CO, $CH_4$, $N_2$ and Ar) is cooled to near ambient in water cooler 235. Condensed water is separated from stream 229 in separator 212. water stream 262 leaving the separator 212 and the cooled water stream 253 leaving the heat exchanger 134 enter a water treatment unit 214, which produces purified water 255 and an excess water stream 261. The purified water 255 functions as the boiler feed-water stream and is pumped to about 87 bar pressure in pump 213. The pressurized boiler feedwater stream 256 leaving the pump 213 enters the heat exchanger 210.

The waste heat boiler feed stream 260 is heated in the waste heat boiler 236 leaving as saturated steam stream 249, which splits into steam stream 250 and quenching stream 223. The saturated steam stream 250 and the preheated natural gas stream 243, both at 290° C. enter a supplemental heat exchanger 237 where they are heated to 500° C. against stream 247, which corresponds to stream 109, the turbine exhaust stream in FIG. 1. The outlet stream 248 enters the recuperative heat exchanger 101 (in the power production unit of FIG. 1) at about 725° C. In this case the inlet temperature for the turbine 103 in the power production unit of FIG. 1 is elevated to provide the required heat transferred in heat exchanger 237, and the turbine power output is increased. The supplemental heat exchanger 237 is thus configured to provide supplemental heating to the saturated steam stream 250 and the natural gas stream 243, the supplemental heating being provided by a stream from the power production unit.

The hot natural gas stream 244 leaving the heat exchanger 237 splits to provide feed at 500° C. to the PDX reactor 201 as stream 246 and to the GHR 202 as stream 245, which mixes with the steam stream 251 to form total GHR feed stream 252. The steam stream 251 fed to the GHR reactor 202 provides a steam to carbon ratio (carbon combined with hydrogen in the GHR reactor feed) of 6:1 in this case. This high ratio allows 80 bar $H_2+CO$ production pressure with a low quantity of unconverted methane in the total product $H_2+CO$ stream 224.

The crude hydrogen product stream 230 leaving the water separator 212 passes into a multi-bed pressure swing adsorption unit 215 that produces a substantially pure $H_2$ product stream 239 with 50 ppm impurity level comprising 88% of the hydrogen present in stream 230. A substantially pure $H_2$ product stream thus can comprise less than 500 ppm impurities, less than 250 ppm impurities, less than 100 ppm impurities, or less than 75 ppm impurities (e.g., down to 0 impurities). The waste stream 232 at 1.2 bar pressure that contains all the $CO_2$ plus various contents of CO, $H_2$, $CH_4$, Argon, $N_2$ and traces of water vapor is compressed to 30 bar in compressor 216 driven by electric motor 219 to leave as stream 238. The discharge stream 238 is cooled in cooler 217 to near ambient and added to the power production system natural gas compressor 105 (see FIG. 1) as part of inlet stream 111 (see FIG. 1). The compressor discharge stream 112 (see FIG. 1) at 320 bar provides the feed to the power production unit combustor 102 (see FIG. 1). The natural gas feed stream 241 at 85 bar can also be produced from a separate natural gas compressor stage, which would be part of the compressor 105 from FIG. 1.

Performance

The integration of a hydrogen production unit operating 246,151 $Nm^3$/hr with a power production cycle system producing 290.3 MW of power, both having pure $CH_4$ or natural gas feed, gives the following calculated performance data.

$H_2$ is produced at 50 ppm total impurity level at a pressure of 74 bar.

Power production=234.23 MW from the integrated system.

$CH_4$ for hydrogen production=92,851.2 $Nm^3$/hr (equal to 923.2 Mw).

$CH_4$ for power production at 43,773.9 $Nm^3$/hr (equal to 435.2 Mw).

Recovery of carbon derived from $CH_4$ feed to the hydrogen plant and power plant, as $CO_2$ is 100%.

$CO_2$ production from the integrated system is 6,437.1 MT/D

The $CO_2$ is produced at 150 bar pressure

In systems and methods as described herein, the use of substantially pure oxygen in the combustor can have the side benefit of providing a large quantity of substantially pure nitrogen. The nitrogen can be provided at relatively high pressure directly from the air separation unit that can be associated with the power production unit to provide the necessary stream of substantially pure oxygen. At least a portion of this nitrogen can be blended with the hydrogen that can be produced as described herein. The end result is an $H_2+N_2$ fuel gas that is suitable for use in a conventional gas turbine combined cycle power generation system. This is exemplified in FIG. 3, wherein nitrogen gas 160 from an air separation unit (see FIG. 1) and hydrogen gas 239 from a hydrogen production facility (see FIG. 2) are input to a gas turbine combined cycle unit 300.

The $H_2+N_2$ fuel gas can be utilized in any gas turbine combined cycle power generation system. Known systems can be modified as necessary to remove, decommission, or otherwise forego the use of elements that would otherwise be required for removal of $CO_2$. Known gas turbine combined cycle power generation systems that can be utilized according to the present disclosure are described in U.S. Pat. No. 8,726,628 to Wichmann et al., U.S. Pat. No. 8,671,688 to Rogers et al., U.S. Pat. No. 8,375,723 to Benz et al., U.S. Pat. No. 7,950,239 to Lilley et al., U.S. Pat. No. 7,908,842 to Eroglu et al., U.S. Pat. No. 7,611,676 to Inage et al., U.S. Pat. No. 7,574,855 to Benz et al., U.S. Pat. No. 7,089,727 to Schutz, U.S. Pat. No. 6,966,171 to Uematsu et al., and U.S. Pat. No. 6,474,069 to Smith, the disclosures of which are incorporated herein by reference.

The combination of systems provided by the present disclosure whereby hydrogen gas and nitrogen gas are provided from a combustion power system wherein a hydrocarbon fuel is combusted with substantially no atmospheric discharge of $CO_2$, provides a distinct advantage over the conventional operation of a gas turbine combined cycle system. In particular, the present combination of systems can eliminate the natural gas fuel typically required in a gas turbine and substitute a fuel with no $CO_2$ production when combusted. As such, in some embodiments, the present disclosure provides a combination of: 1) an oxygen based hydrogen production unit; 2) a power generation unit that captures substantially all of the $CO_2$ produced; and a conventional gas turbine combined cycle power generation unit that provides for additional power generation. Combined systems as described herein can provide a surprisingly high efficiency, low cost power generation, and approximately 100% $CO_2$ capture. The result is thus a heretofore unknown manner for providing power production from natural gas combustion with approximately 100% $CO_2$ capture and operating costs that are equal to or lower than known power productions methods that do not provide for 100% $CO_2$ capture.

The combination of systems can be implemented in a variety of manners. In some embodiments, an existing combined cycle power station can be converted to eliminate all $CO_2$ emissions and simultaneously increase the power generation capacity. Such conversion can include addition of the further system components described herein for production of power using a $CO_2$ circulating fluid and production of $H_2+N_2$ fuel gas.

Performance

Performance calculations for a combined system as described above can be based on a GE PG9371(FB) gas turbine cogeneration system that is adapted to produce 432.25 Mw of power at iso conditions. Calculated values according to embodiments of the present disclosure are provided below considering the combination of a natural gas combustion power production unit with 100% $CO_2$ capture, $H_2$ production, $N_2$ production, and combustion of $H_2+N_2$ fuel gas in the gas turbine.

Total net power production from the combined system is 697 Mw

Fuel to the gas turbine is assumed to be 50% $H_2$+50% $N_2$ (molar)

Total methane feed is 1,368.6 Mw (LHV)

Oxygen required is 4979 MT/day $CO_2$ produced at 150 bar pressure is 6,437 Mt/day Overall efficiency is 50.9% (LHV basis)

Many modifications and other embodiments of the presently disclosed subject matter will come to mind to one skilled in the art to which this subject matter pertains having the benefit of the teachings presented in the foregoing descriptions and the associated drawings. Therefore, it is to be understood that the present disclosure is not to be limited to the specific embodiments described herein and that modifications and other embodiments are intended to be included within the scope of the appended claims. Although specific terms are employed herein, they are used in a generic and descriptive sense only and not for purposes of limitation.

The invention claimed is:

1. A method for hydrogen production from a carbonaceous fuel with capture of carbon dioxide derived from the carbonaceous fuel, the method comprising:

reacting a first portion of the carbonaceous fuel from a carbonaceous fuel stream in a first reactor with oxygen under conditions effective to produce a first reaction stream comprising hydrogen and carbon monoxide;

reacting a second portion of the carbonaceous fuel from the carbonaceous fuel stream in a second reactor with steam under conditions effective to produce a second reaction stream comprising hydrogen and carbon monoxide, wherein the reacting in the second reactor is endothermic, and wherein exhaust heat from the first reactor is transferred to the second reactor to provide at least a portion of the heating needed to carry out the reacting in the second reactor;

combining the first reaction stream comprising hydrogen and carbon monoxide with the second reaction stream comprising hydrogen and carbon monoxide to provide a total reaction stream comprising hydrogen and carbon monoxide;

processing the total reaction stream comprising hydrogen and carbon monoxide through a unit or units effective to provide a stream of substantially pure hydrogen and a waste stream comprising at least carbon dioxide;

providing the waste stream comprising the at least carbon dioxide to a combustor in a power production cycle configured for capture of the carbon dioxide in combination with power production, the combustor being configured for combusting a third portion of the carbonaceous fuel from the carbonaceous fuel stream with oxygen under conditions effective to produce a combustor exhaust stream comprising at least carbon dioxide; and processing the combustor exhaust stream comprising the at least carbon dioxide so that the carbon dioxide from the combustor exhaust stream is provided as a compressed, substantially pure stream.

2. The method of claim 1, wherein the conditions effective to produce the combustor exhaust stream include providing the combustor exhaust stream at a sufficiently high temperature so that the combustor exhaust stream is used to heat one or more of the fuel from the carbonaceous fuel stream that is input to the first reactor, the fuel from the carbonaceous fuel stream that is input to the second reactor, and the steam that is input to the second reactor.

3. The method of claim 2, wherein the one or more of the fuel from the carbonaceous fuel stream that is input to the first reactor, the fuel from the carbonaceous fuel stream that is input to the second reactor, and the steam that is input to the second reactor is heated to a temperature greater than 290° C.

4. The method of claim 3, wherein the one or more of the fuel from the carbonaceous fuel stream that is input to the first reactor, the fuel from the carbonaceous fuel stream that is input to the second reactor, and the steam that is input to the second reactor is heated to the a-temperature of about 400° C. to about 550° C.

5. The method of claim 2, wherein the combustor exhaust stream comprising the least carbon dioxide is passed through a turbine for the power production.

6. The method of claim 5, wherein the combustor exhaust stream is used to heat one or more of the fuel from the carbonaceous fuel stream that is input to the first reactor, the fuel from the carbonaceous fuel stream that is input to the second reactor, and the steam that is input to the second reactor after being passed through the turbine.

7. The method of claim 2, wherein the combustor exhaust stream exiting a the-turbine is passed through a second combustor where a fourth portion of the carbonaceous fuel from the carbonaceous fuel stream, or a different fuel, is combusted with oxygen to provide further heat to the combustor exhaust stream exiting the turbine.

8. The method of claim 2, wherein the combustor exhaust stream exiting a the turbine is combined with a preheated stream of the carbonaceous fuel from the carbonaceous fuel stream, or a different fuel, and passed through an ion transport membrane combustor that also receives a stream of preheated low-pressure air.

9. The method of claim 1, wherein the first reaction stream comprising hydrogen and carbon monoxide is combined with the second reaction stream comprising hydrogen and carbon monoxide in the second reactor so that the total reaction stream comprising hydrogen and carbon monoxide is provided as an output from the second reactor.

10. The method of claim 1, wherein the first reactor is a partial oxidation reactor or an auto-thermal reactor.

11. The method of claim 1, wherein the second reactor is a gas heated reformer.

12. The method of claim 1, wherein processing the total reaction stream comprising hydrogen and carbon monoxide comprises passing the processing the total reaction stream comprising hydrogen and carbon monoxide through a waste heat boiler wherein heat from the total reaction stream comprising hydrogen and carbon monoxide is used to heat a feed-water stream.

13. The method of claim 1, wherein the processing the total reaction stream comprising hydrogen and carbon monoxide includes passing the total reaction stream comprising hydrogen and carbon monoxide through one or more catalytic shift reactors where carbon monoxide present in the total reaction stream comprising hydrogen and carbon monoxide reacts with steam present in the total reaction stream comprising hydrogen and carbon monoxide to produce the carbon dioxide and the hydrogen and produce a shift stream comprising at least carbon dioxide and hydrogen.

14. The method of claim 13, wherein the total reaction stream comprising hydrogen and carbon monoxide that initially enters the one or more catalytic shift reactors contains about 20% to about 40% steam on a molar basis based on the overall composition of the total reaction stream comprising hydrogen and carbon monoxide.

15. The method of claim 13, further comprising passing the shift stream comprising at least carbon dioxide and hydrogen through one or more shift stream heat recovery heat exchangers so that heat from the shift stream comprising at least carbon dioxide and hydrogen is used to heat one or more of the fuel from the carbonaceous fuel stream that is input to the first reactor, the fuel from the carbonaceous fuel stream that is input to the second reactor, and feed-water that forms the steam that is input to the second reactor.

16. The method of claim 15, further comprising removing water from the shift stream comprising at least carbon dioxide and hydrogen and processing the water in a water purifier to form a boiler feed-water stream.

17. The method of claim 15, further comprising passing the shift stream comprising at least carbon dioxide and hydrogen through a pressure swing adsorption unit to produce the stream of substantially pure hydrogen and the waste stream comprising at least carbon dioxide.

18. The method of claim 17, wherein the waste stream comprising at least carbon dioxide is compressed and then added to the third portion of the carbonaceous fuel from the carbonaceous fuel stream that is combusted with oxygen in the combustor of the power production cycle.

19. The method of claim 15, wherein passing the shift stream comprising at least carbon dioxide and hydrogen through one or more shift stream heat recovery heat exchangers is effective to heat the feed-water that forms the steam that is input to the second reactor, and wherein a portion of the feed-water that is heated is divided and passed through a heat exchanger to add heat to a further stream.

20. The method of claim 19, wherein the further stream is a stream in the power production cycle.

21. A method for hydrogen production from a carbonaceous fuel with capture of carbon dioxide derived from the carbonaceous fuel, the method comprising:

reacting a first portion of the carbonaceous fuel from a carbonaceous fuel stream in a first reactor with oxygen under conditions effective to produce a first reaction stream comprising hydrogen and carbon monoxide;

reacting a second portion of the carbonaceous fuel from the carbonaceous fuel stream in a second reactor with steam under conditions effective to produce a second reaction stream comprising hydrogen and carbon monoxide;

combining the first reaction stream comprising hydrogen and carbon monoxide with the second reaction stream comprising hydrogen and carbon monoxide to provide a total reaction stream comprising hydrogen and carbon monoxide;

processing the total reaction stream comprising hydrogen and carbon monoxide through one or more catalytic shift reactors where carbon monoxide present in the total reaction stream comprising hydrogen and carbon monoxide reacts with steam present in the total reaction stream comprising hydrogen and carbon monoxide to produce carbon dioxide and hydrogen and thus produce a shift stream comprising at least carbon dioxide and hydrogen;

passing the shift stream comprising at least carbon dioxide and hydrogen through one or more shift stream heat recovery heat exchangers so that heat from the shift stream comprising at least carbon dioxide and hydrogen is used to heat one or more of the fuel from the carbonaceous fuel stream that is input to the first reactor, the fuel from the carbonaceous fuel stream that is input to the second reactor, and feed-water that forms the steam that is input to the second reactor;

processing the shift stream comprising at least carbon dioxide and hydrogen through a unit or units effective to provide a stream of substantially pure hydrogen and a waste stream comprising at least carbon dioxide;

providing the waste stream comprising the at least carbon dioxide to a combustor in a power production cycle configured for capture of the carbon dioxide in combination with power production, the combustor being configured for combusting a third portion of the carbonaceous fuel from the carbonaceous fuel stream with oxygen under conditions effective to produce a combustor exhaust stream comprising at least carbon dioxide; and processing the combustor exhaust stream comprising the at least carbon dioxide so that the carbon dioxide from the combustor exhaust stream is provided as a compressed, substantially pure stream.

\* \* \* \* \*